(12) United States Patent
Ko et al.

(10) Patent No.: US 9,782,447 B2
(45) Date of Patent: Oct. 10, 2017

(54) **METHOD TO PREPARE *HIRSUTELLA SINENSIS* POLYSACCHARIDES POSSESSING PROTECTIVE ACTIVITIES ON FATTY LIVER DISEASE**

(71) Applicant: Chang Gung Biotechnology Corp., Taipei (TW)

(72) Inventors: Yun-Fei Ko, Taipei (TW); Jan Martel, Taipei (TW); Jian-Ching Liau, Taipei (TW); I-Te Chang, Taipei (TW); Chien-Sheng Lee, Taipei (TW); Wei-Chang Wang, Taipei (TW); Chen-Yaw Chiu, Taipei (TW); Chih-Jung Chang, Taipei (TW); Chuan-Sheng Lin, Taipei (TW); Tsung-Ru Wu, Taipei (TW); Chia-Chen Lu, Taipei (TW); David Marcelo Ojcius, Taipei (TW); Hsin-Chih Lai, Taipei (TW); Ding-E Young, Taipei (TW)

(73) Assignee: Chang Gung Biotechnology Corp., Taipei (TW)

( * ) Notice: Subject to any disclaimer, the term of this patent is extended or adjusted under 35 U.S.C. 154(b) by 58 days.

(21) Appl. No.: 14/856,425

(22) Filed: Sep. 16, 2015

(65) Prior Publication Data

US 2016/0361370 A1    Dec. 15, 2016

(30) Foreign Application Priority Data

Jun. 11, 2015 (TW) .............................. 104118929 A

(51) Int. Cl.
*A61K 36/06* (2006.01)
*A61K 31/715* (2006.01)
*A61K 31/7004* (2006.01)
*A61K 31/7008* (2006.01)

(52) U.S. Cl.
CPC .......... *A61K 36/06* (2013.01); *A61K 31/7004* (2013.01); *A61K 31/7008* (2013.01); *A61K 31/715* (2013.01)

(58) Field of Classification Search
CPC .............................. A61K 36/06; A61K 31/715
See application file for complete search history.

(56) References Cited

PUBLICATIONS

Mayo Clinic, Nonalcoholic fatty liver disease web page, http://www.mayoclinic.org/diseases-conditions/nonalcoholic-fatty-liver-disease, accessed online on Mar. 1, 2017.*
WebMD, Fatty liver disease web page, http://www.webmd.com/hepatitis/fatty-liver-disease, accessed online on Mar. 1, 2017.*
Definition of prevent, Oxford English Dictionary Online, http://dictionary.oed.com/, accessed online Mar. 27, 2010, especially definition 9a. at p. 2.*
Koh et al., Biol. Pharm. Bull., 2003, 26(1), p. 84-87.*
Primordia World of Mushrooms website, http://www.primordiamushrooms.com/our-products/cordyceps-sinensis/, accessed online on Feb. 8, 2017.*
Marchesini et al., Diabetes, 2001, 50, p. 1844-1850.*

* cited by examiner

*Primary Examiner* — Jonathan S Lau
(74) *Attorney, Agent, or Firm* — WPAT, P.C., Intellectual Property Attorneys; Anthony King

(57) ABSTRACT

The present invention provides a method to prepare polysaccharides from *Hirsutella sinensis*. The prepared polysaccharides can reduce liver size, weight and the number and size of liver lipid vacuoles, as well as serum triglycerides and serum aspartate aminotransferase levels in humans and animals. The prepared polysaccharides can therefore be used to prevent and treat fatty liver disease.

8 Claims, 10 Drawing Sheets

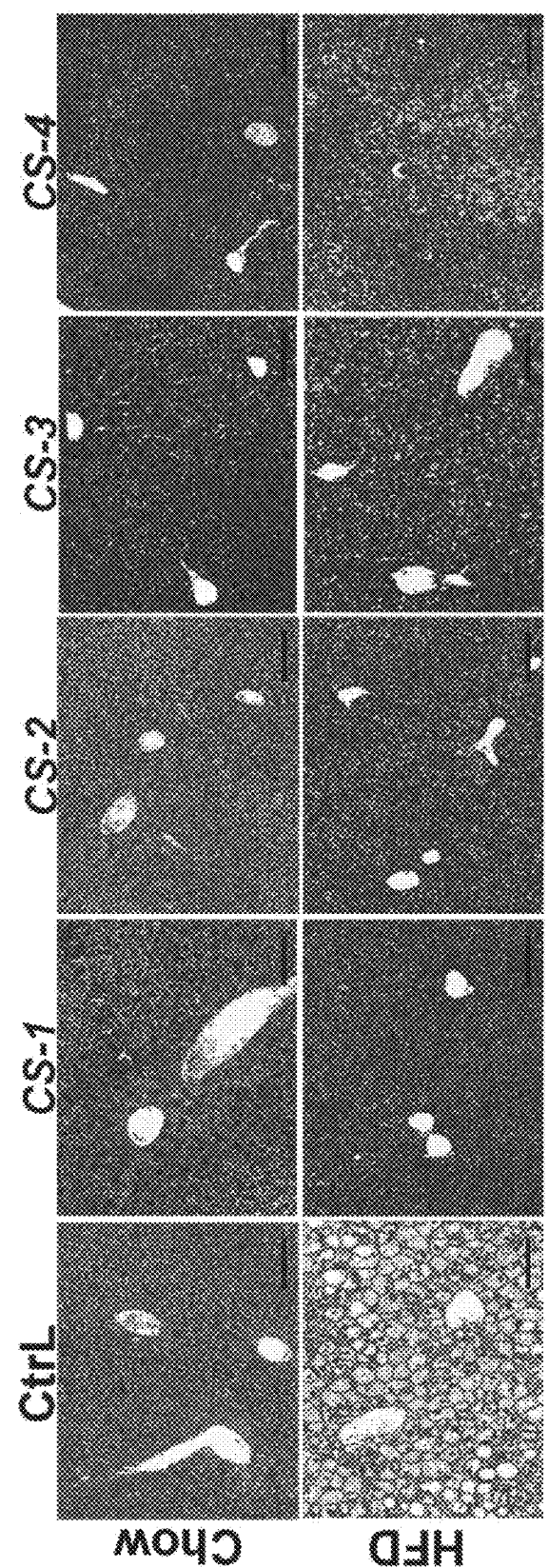

METHOD TO PREPARE *HIRSUTELLA SINENSIS* POLYSACCHARIDES POSSESSING PROTECTIVE ACTIVITIES ON FATTY LIVER DISEASE

CROSS-REFERENCE TO RELATED APPLICATION

This application claims priority of Taiwan patent application No. 104118929, filed on Jun. 11, 2015, the content of which is incorporated herein in its entirety by reference.

BACKGROUND OF THE INVENTION

1. Field of the Invention

The present invention relates to compositions and methods for preventing and treating fatty liver disease. Particularly, the present invention provides methods for preventing and treating fatty liver disease by using polysaccharides isolated from *Hirsutella sinensis* as well as methods for preparing the polysaccharides.

2. The Prior Art

Traditional Chinese medicine has a long history in Asian countries dating back several thousands of years. One class of traditional remedies commonly in use consists of medicinal mushrooms such as *Antrodia cinnamomea*, *Agaricus blazei* Murrill, *Ganoderma lucidum*, and *Ophiocordyceps sinensis*. These mushrooms contain a wide range of immuno-modulatory and bioactive compounds. The medicinal mushroom *Ophiocordyceps sinensis* has been used for centuries to promote health and longevity. Recent work has identified that the anamorph (i.e., mycelium) of *O. sinensis* fruiting bodies is *Hirsutella sinensis*. Previous studies have shown that extracts of *O. sinensis* fruiting bodies and *H. sinensis* mycelium produce various effects on laboratory animals, including anti-fatigue, kidney-protecting, and libido-enhancing effects.

Fatty liver disease is a condition in which large vacuoles of triglycerides accumulate in the liver. This condition occurs mostly in the liver of alcoholic and obese individuals. Fatty liver disease is often associated with inflammation, a condition termed steatohepatitis. In the long term, fatty liver disease may lead to several complications, including liver cirrhosis, hepatocellular carcinoma, and death. The high prevalence of fatty liver disease is currently a major threat to public health, with an estimated 10 to 24% of the human population being affected worldwide. Prevention and treatment of this disease thus represents a major challenge.

In view of the growing incidence of fatty liver disease in the human population and the difficulties observed in prevention and treatment, there is a need for alternative measures to prevent, treat and control this condition. New measures that can be introduced in the diet without requiring considerable changes in lifestyle and without incurring in toxicity or adverse effects on health are particularly needed.

SUMMARY OF THE INVENTION

The present invention provides a method for preventing or treating fatty liver disease comprising the administration of an effective amount of a polysaccharide extracted from *Hirsutella sinensis* to a subject, wherein the polysaccharide is isolated from a water extract of a *H. sinensis* mycelium and contains at least mannose, galactose, and glucose.

In one embodiment of the present invention, the polysaccharide further contains fucose, rhamnose, arabinose, glucosamine, and galactosamine.

In one embodiment of the present invention, the weight ratio of fucose, rhamnose, arabinose, glucosamine, galactose, glucose, mannose, and galactosamine in the polysaccharide is 3:3:1:4:23:12:50:0.2 to 4:4:2:5:24:13:51:0.6.

In one embodiment of the present invention, the polysaccharide has a molecular weight ranging from 15,776 Da to 1,231,969 Da, an average molecular weight of 312 kDa, and a polydispersity index of 7.475.

The *H. sinensis* polysaccharide of the present invention reduces liver weight and liver vacuolation in a subject. In addition, the *H. sinensis* polysaccharide of the present invention reduces serum triglycerides (TG) and serum aspartate aminotransferase (AST) levels of the subject. In one embodiment of the present invention, the effective amount of the polysaccharide is from 0.001 mg/kg to 1 g/kg. Preferably, the effective daily amount or dosage of *G. lucidum* polysaccharide given to a human subject (with an average weight of 70 kg) is 4.53 g (0.0646 g per kilogram of body weight).

The present invention also provides a method for preparing the *H. sinensis* polysaccharide sub-fraction, comprising: extracting *H. sinensis* mycelium with water; inducing the formation of a precipitate by adding an alcohol; separating the precipitate by centrifugation; and fractionating the precipitate by filtration, wherein, (a) mixing the *H. sinensis* mycelium with water to give a first mixture, incubating the first mixture for a first predetermined time under a low-speed rotation, centrifugating the first mixture to give a supernatant, and concentrating the supernatant to obtain a concentrated *H. sinensis* water extract; (b) adding an alcohol to to give a second mixture, incubating the second mixture for a second predetermined time to obtain a precipitate of crude *H. sinensis* polysaccharide; (c) isolating the precipitate of crude *H. sinensis* polysaccharide by centrifugation, and fractionating the polysaccharide using tangential flow filtration (TFF) to obtain a *H. sinensis* polysaccharide sub-fraction possessing anti-fatty liver activities.

In one embodiment of the present invention, for step (a), the *H. sinensis* mycelium is mixed with water at a weight ratio of 5% (w/v) and the supernatant is concentrated using a vacuum concentrator. For step (b), the alcohol is 95% ethanol, each volume of the concentrated *H. sinensis* water extract is mixed with five volumes of 95% ethanol, and the second predetermined time is at least 16 hours. For step (c), the crude *H. sinensis* polysaccharide extract is fractionated using TFF with a 0.2-μm hollow fiber membrane and 10-to-300-kDa cassette membranes (50 cm$^2$, polyethersulfone, PES).

The *H. sinensis* polysaccharide of the present invention can reduce liver weight, liver vacuolation, serum TG and serum AST levels in humans and animals. Therefore, the polysaccharides can be used as a drug, health supplement or food for preventing or treating fatty liver disease.

BRIEF DESCRIPTION OF THE DRAWINGS

The nature of the present invention will be apparent to those skilled in the art by reading the following detailed description of the preferred embodiments, with reference to the attached drawings:

FIGS. 6A-6E show the effects of *H. sinensis* polysaccharide sub-fractions on fatty liver disease in mice. Male C57BL/6 mice (n=10 per group) are fed with either standard chow (13.5% of energy from fat) or high-fat diet (HFD, 60% of energy from fat). The mice are supplemented with 10 μL of polysaccharide fraction (CS-1, CS-2, CS-3, or CS-4) or double-distilled water for 3 months by intragastric gavage. FIG. 6A shows the mice are sacrificed and livers are photographed; scale bars: 5 mm FIG. 6B shows the livers of mice are weighted. FIG. 6C shows the Liver tissue slides are prepared and stained with hematoxylin and eosin (H&E) to assess histological features; scale bars: 20 μm. FIG. 6D shows the determined serum TG level. FIG. 6E shows the determined serum AST levels. The results show that CS-1, CS-2 and CS-3 reduce signs of fatty liver disease in HFD mice compared to control HFD mice (***$p<0.001$, one-way ANOVA; ns, non-significant). CS-4 improves liver weight, vacuolation status, and serum TG levels compared to control HFD mice, but this sub-fraction produces non-significant results on serum AST levels. The results shown represent means±standard error of the mean (SEM).

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

The "effective dosage" or "effective amount" described in the present disclosure represents the dosage of *H. sinensis* polysaccharide sub-fraction that can reduce signs of fatty liver disease in animals and humans. The appropriate effective dosage may vary depending on the organism or individual treated but can be determined experimentally using various techniques, including a dose escalation study.

The data shown in the present disclosure represent approximated experimental values that can vary within a range of ±20%, preferably ±10%, and most preferably ±5%.

The present invention provides *H. sinensis* polysaccharide sub-fractions which are able to prevent or treat fatty liver disease, and the embodiments below show that the *H. sinensis* polysaccharides of the present invention reduce liver weight, vacuolation status, serum TG and serum AST levels of a subject. Generally, the polysaccharides of the present invention can be given to mammals and humans at a dose of 0.001-1,000 mg/kg of body weight per day. The details of the invention are given below.

Characterization of the *H. sinensis* polysaccharide of the present invention is presented first, followed by experimentations showing that the isolated *H. sinensis* polysaccharide sub-fractions reduce signs of fatty liver disease.

Example 1

Preparation of *H. sinensis* Water Extracts and Polysaccharide Sub-Fractions In the present invention, the polysaccharide sub-fractions isolated from *H. sinensis* can effectively reduce liver weight, liver vacuolation, serum TG and AST levels. The polysaccharide sub-fractions of the present invention can be added to the diet as a drink, daily supplement, or food, without requiring significant lifestyle change, or without incurring in toxicity or other unfavorable health conditions.

1.1 Preparation of *H. sinensis* Water Extracts

Figure 1:
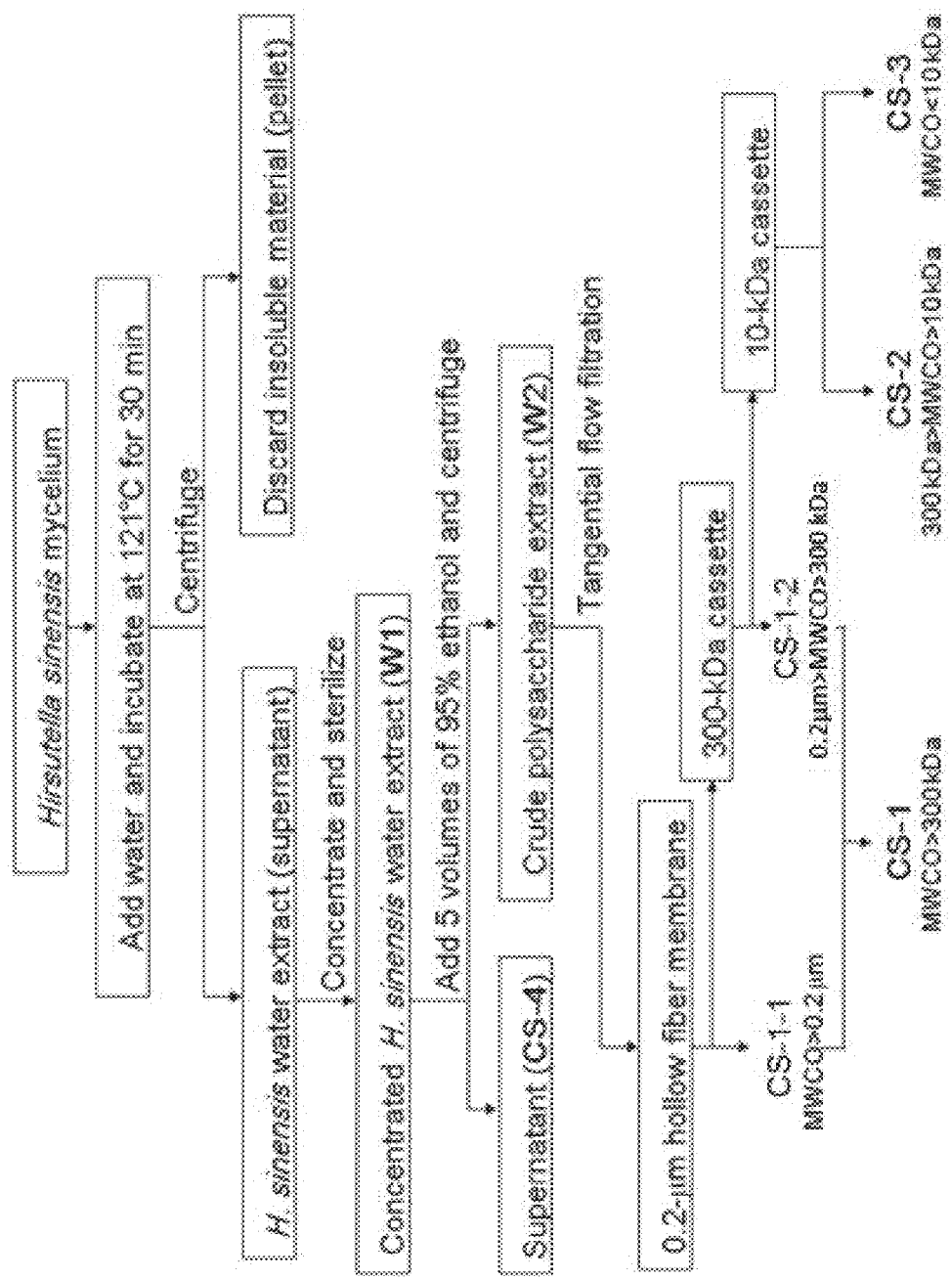
FIG. 1 shows a simplified flowchart for the isolation of the *H. sinensis* water extracts and polysaccharide sub-fractions described in the present invention.

As shown in FIG. 1, a water extract is prepared by mixing 500 g of *H. sinensis* mycelium obtained from Chang Gung Biotechnology (Taipei, Taiwan) into 10 liters of distilled water using a 20 liter-stirred tank reactor. The 5% (w/v) mixture is agitated at a speed of 150 revolutions per minute (RPM) for 30 min at 121° C. The mixture is centrifuged to remove insoluble material and to obtain a supernatant (water extract of *H. sinensis*). The supernatant is concentrated to a final volume of 2.5 liters using a vacuum concentrator. The concentrated supernatant is sterilized at high temperature and pressure for 20 min in an autoclave to obtain a 20% (w/v) concentrated *H. sinensis* water extract labeled as W1 (FIG. 1).

1.2 Preparation of *H. sinensis* Crude Polysaccharide Extract

Referring to FIG. 1, 120 mL of the W1 20% (w/v) concentrated *H. sinensis* water extract (which contains 2.09 g of total water-soluble carbohydrates; see Table 1) is mixed with 5 volumes (600 mL) of 95% ethanol and incubated at 4° C. for 16 hours to obtain a precipitate of crude polysaccharide extract. The mixture is centrifuged to isolate the precipitate (pellet). The supernatant is removed and 120 mL of 70% ice-cold ethanol is used to wash and resuspend the precipitate (pellet) and obtain a mixture. The mixture is centrifuged to obtain a supernatant and a pellet. The supernatants from three such washing-resuspension-centrifugation steps are combined to give a supernatant with a volume of 1,040 mL (labeled as sub-fraction CS-4, total water-soluble carbohydrates of 0.83 g; see Table 1). The crude polysaccharide extract is dissolved into 1,000 mL of distilled water and concentrated to a final volume of 700 mL using the vacuum concentrator in order to remove residual ethanol. Finally, distilled water is added to obtain a *H. sinensis* crude polysaccharide extract with a final volume of 2,400 mL (labeled as W2, total water-soluble polysaccharide of 1.26 g; see Tables 1 and 2).

1.3 Fractionation of *H. sinensis* Crude Polysaccharide Extract 2,400 mL of *H. sinensis* crude polysaccharide extract is placed into a beaker and incubated at 50° C. in a water bath. The extract is fractionated by using TFF system (KrosFlo, Spectrum Laboratories) with a 0.2-μm hollow fiber membrane (1,500 cm$^2$, PES). The trans-membrane pressure (TMP) is set at 15-16 psi. 600 mL of distilled water is added into the retentate during filtration when the volume of the retentate ranges from 800 to 1,000 mL. Addition of water is repeated two times (a total of 1,800 mL distilled water is added to the retentate). A 1,250 mL retentate (labeled as CS-1-1, total water-soluble polysaccharide of 0.24 g) and 3,600 mL of filtrate are obtained this way.

The above-mentioned 3,600 mL of 0.2-μm filtrate is placed into a beaker and incubated at 50° C. in a water bath. The 3,600 mL of filtrate is fractionated by using TFF as above with a 300-kDa cassette membrane (50 cm², PES). The TMP is set between 18-20 psi. 600 mL of distilled water is added into the retentate during filtration when the volume of the retentate ranges from 1,000 mL to 1,200 mL. 1,040 mL of retentate (labeled as CS-1-2, total water-soluble polysaccharide of 0.18 g) and 3,600-mL filtrate are obtained. Fractions CS-1-1 and CS-1-2 are combined to obtain a volume of 2,290 mL (labeled as sub-fraction CS-1, which contains 0.42 g of total water-soluble polysaccharides; see Table 2).

The above-mentioned 3,600 mL of 300-kDa filtrate is placed into a beaker and the latter is incubated at 50° C. in a water bath. The 300-kDa filtrate is fractioned using TFF with a 10-kDa cassette membrane (50 cm², PES). The TMP is set between 18-20 psi. 600 mL of distilled water is added into the retentate during filtration when the retentate ranges between 1,000 mL and 1,200 mL. The operation is repeated to obtain 990 mL of 10-kDa-to-300-kDa retentate (labeled as sub-fraction CS-2, containing 0.64 g of total water-soluble polysaccharides; see Table 2) and 3,600 mL of 10-kDa filtrate (labeled as sub-fraction CS-3, total water soluble polysaccharides of 0.16 g; see Table 2).

The CS-1, CS-2, CS-3 and CS-4 fractions are concentrated separately using a vacuum concentrator to obtain a final volume of 120 mL. Concentrated fractions are sterilized at 121° C. for 20 min in an autoclave and stored at 4° C.

1.4 Determination of Total Water-Soluble Carbohydrates and Polysaccharides in *H. Sinensis* Water Extracts and Polysaccharide Sub-Fractions The phenol-sulfuric acid assay is used to determine the level of total water-soluble carbohydrates and polysaccharides in the water extracts and polysaccharide sub-fractions isolated from *H. sinensis*, including: the W1 20% (w/v) concentrated *H. sinensis* water extract (120 mL), the W2 *H. sinensis* crude polysaccharide extract (2400 mL), a combination of the retentate of the 0.2-μm filtration and 300-kDa-cutoff filtration (labeled as CS-1 sub-fraction; 2,290 mL), the retentate of the 10-kDa membrane filtration (labeled as CS-2; 990 mL), the filtrate of the 10-kDa-cutoff membrane filtration (labeled as CS-3; 3,600 mL), and the supernatants of the 95% ethanol precipitation and washing steps (labeled as sub-fraction CS-4; 1,040 mL). To establish a standard curve for the phenol-sulfuric acid assay, glucose standard solutions are prepared at concentrations of 0, 0.02, 0.04, 0.06, 0.08, 0.10, 0.12, 0.14, 0.16, 0.18, and 0.20 mg/mL. 200 μL of each solution is placed into 1.5-mL tubes. 200 μL of 5% phenol is added and the solution is mixed. 1 mL of sulfuric acid is added and the solution is mixed. After incubation for 20 min, absorbance is monitored at 490 nm using a spectrophotometer. The calibration curve of glucose standard solutions is prepared (calculated $R^2$>0.99). The sample solutions are appropriately diluted. 200 μL of each diluted solution is placed into 1.5-mL tubes. Phenol and sulfuric acid are added and absorbance is monitored as above. The values obtained are plotted onto the calibration curve of glucose standard solutions to determine the concentration of total water-soluble carbohydrates or polysaccharide of the samples.

Total water-soluble carbohydrates and polysaccharides measured in the extracts and sub-fractions isolated from *H. sinensis* are shown in Tables 1 and 2. The analysis in Table 2 shows that the W2 crude polysaccharide extract contains 0.42 g of total water-soluble polysaccharides with a molecular weight above 300 kDa (CS-1), which accounts for 33.3% of the total polysaccharides found in the *H. sinensis* crude polysaccharide extract (W2). The W2 extract also contains 0.64 g of polysaccharides between 10 kDa to 300 kDa (CS-2), which accounts for 50.8% of the total polysaccharides found in the W2 extract. The W2 extract also contains 0.16 g of polysaccharides with a molecular weight below 10 kDa (CS-3), which accounts for 12.7% of the total polysaccharides found in the W2 extract.

TABLE 1

Determination of water-soluble carbohydrates and polysaccharides in water extracts and CS-4 polysaccharide sub-fraction isolated from *H. sinensis*

| Fraction | | Content (g) | Percentage (%) |
|---|---|---|---|
| W1 | Total water-soluble carbohydrates | 2.09 | 100 |
| W2 | Total water-soluble polysaccharides | 1.26 | 60.3 |
| CS-4 | Mono-, di-, oligo-saccharides | 0.83 | 39.7 |

TABLE 2

Polysaccharide distribution of W2 concentrated water extract and polysaccharide sub-fractions isolated from *H. sinensis*

| Fraction | | Content (g) | Percentage (%) |
|---|---|---|---|
| W2 | Total water-soluble carbohydrates | 1.26 | 100 |
| CS-1 | MWCO > 300 kDa | 0.42 | 33.3 |
| CS-2 | 300 kDa > MWCO > 10 kDa | 0.64 | 50.8 |
| CS-3 | 10 kDa > MWCO | 0.16 | 12.7 |

MWCO: Molecular Weight Cut-Off 1.5 Monosaccharide Composition of the CS-1 Polysaccharide Sub-Fraction High pH anion exchange chromatography-pulsed amperometric detection (HPAEC-PAD) is used to analyze the monosaccharide composition of the CS-1 sub-fraction, which is selected here as a representative polysaccharide sub-fraction possessing insulin-sensitizing effects. Monosaccharide standard solutions of L-fucose, L-rhamnose, D-galactosamine, D-arabinose, D-glucosamine, D-galactose, D-glucose and D-mannose are prepared at 0.1, 0.5, 1, 2, and 5 mg/L. 25 μL of each solution is submitted to ionic chromatography analysis with the HPAEC-PAD Dionex ICS-5000 System (CarboPacPA1 column with an internal diameter of 4×250 mm; Thermo Scientific). Elution is performed with 16 mM NaOH (which corresponds to a mixture of water and 200 mM NaOH at the volume ratio of 92:8). The flow rate is set at 1 mL/min. Temperature of column is set at 30° C. After 30 min of analysis, the peak area of each monosaccharide standard is determined and the standard curve of monosaccharide standards is prepared ($R^2$>0.99).

Figure 2:
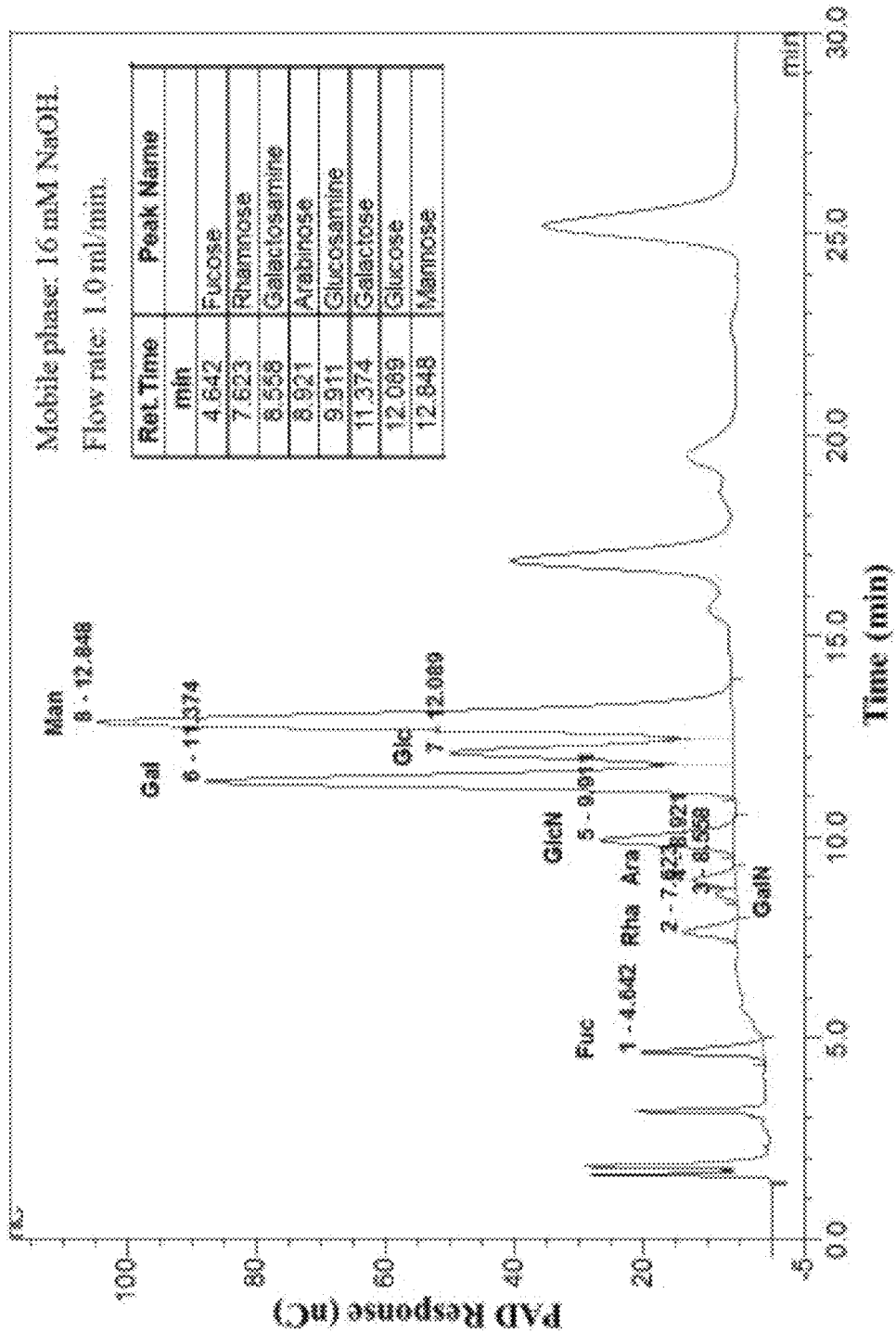
FIG. 2 shows the monosaccharide analysis of *H. sinensis* polysaccharide sub-fraction CS-1. The analysis was performed using high-performance anion exchange chromatography with pulsed amperometric detection (HPAEC-PAD).

1 mL of CS-1 sub-fraction (containing 3 mg of total water-soluble polysaccharides) is hydrolyzed with 1.79 mL of distilled water and 1.33 mL of trifluoroacetic acid at 112° C. for 12 hours. Acid is removed by co-distillation with water after the hydrolysis is complete. Each hydrolysate (1 mg) is dissolved in pure water (1 mg/mL). After a 4-fold dilution of the hydrolysate with pure water (0.25 mg/mL), 25 μL of the hydrolysate solution is used for ionic chromatography analysis using the HPAEC-PAD system. Elution is performed as above. After 30 min of analysis, the analytic HPAEC-PAD profile of hydrolysate solution is acquired. The monosaccharide composition and molar ratio of the CS-1 sub-fraction is determined by comparison with the standard curve. The CS-1 sub-fraction is found to contain 3.2% fucose, 3.4% rhamnose, 1.7% arabinose, 4.6% glucosamine, 23.8% galactose, 12.5% glucose, 50.4% mannose, and 0.4% galactosamine (Tables 3 and 4 and FIG. 2).

TABLE 3

Monosaccharide composition of CS-1 polysaccharide sub-fraction isolated from *H. sinensis* and analyzed using HPAEC-PAD

| Monosaccharide | Percentage (%) |
|---|---|
| Fucose | 3.2 |
| Rhamnose | 3.4 |
| Arabinose | 1.7 |
| Glucosamine | 4.6 |
| Galactose | 23.8 |
| Glucose | 12.5 |
| Mannose | 50.4 |
| Galactosamine | 0.4 |

TABLE 4

Monosaccharide molar ratio of CS-1 polysaccharide sub-fraction isolated from *H. sinensis*

| Monosaccharide | Molar ratio |
|---|---|
| Fucose | 0.07 |
| Rhamnose | 0.07 |
| Arabinose | 0.04 |
| Glucosamine | 0.09 |
| Galactose | 0.47 |
| Glucose | 0.25 |
| Mannose | 1 |
| Galactosamine | 0.01 |

1.6 Molecular Weight Distribution of CS-1 and CS-2 Polysaccharide Sub-Fractions Isolated from *H. sinensis*

The molecular weights of the CS-1 and CS-2 sub-fractions are analyzed by size-exclusion chromatography (SEC) and high performance liquid chromatography with a refractive index detector (Waters, model 2410) and a dual detector (Viscotek, model 270). Dextran 670 (1.5 mg/mL) is used as a standard marker to calibrate the system. 100 μL of sample is analyzed on two connected GPC columns (TSKgel G5000PWxL and TSKgel G6000PWxL; 7.8×300 mm) Elution is performed with 0.02% NaNO$_3$ in pure water. The flow rate is set at 0.5 mL/min (column temperature of 45° C.).

Molecular weight parameters of the CS-1 and CS-2 sub-fractions are calculated using the OmniSEC software (Viscotek) and the following equations:

Mn: number average molecular weight $$Mn = \frac{\sum NiMi}{\sum Ni}$$

Mw: weight average molecular weight $$Mw = \frac{\sum NiMi^2}{\sum NiMi}$$

Mz: higher average molecular weight $$Mz = \frac{\sum NiMi^3}{\sum NiMi^2}$$

Figure 3:
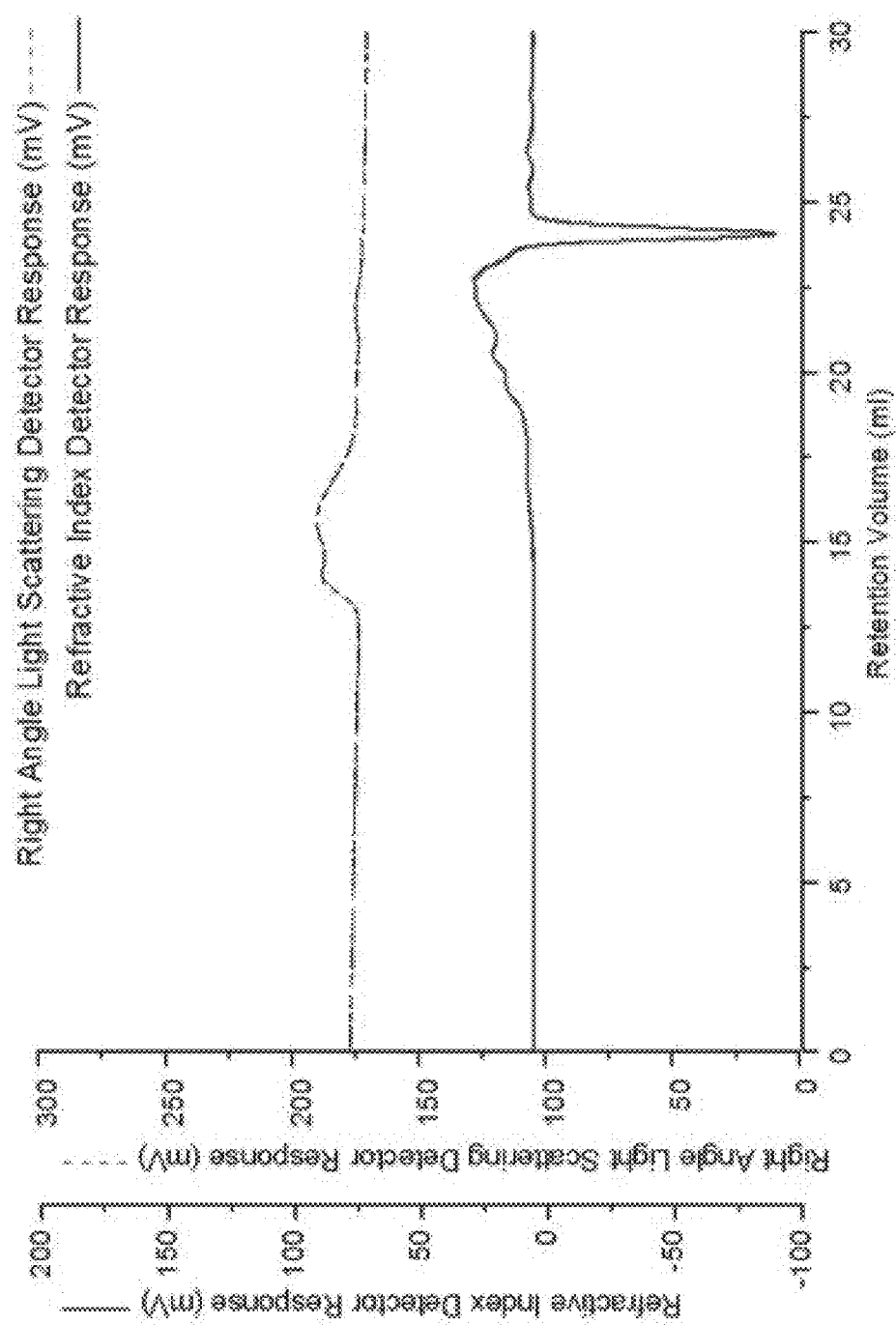
FIG. 3 shows the gel permeation chromatogram of *H. sinensis* polysaccharide sub-fraction CS-1.
Figure 4:
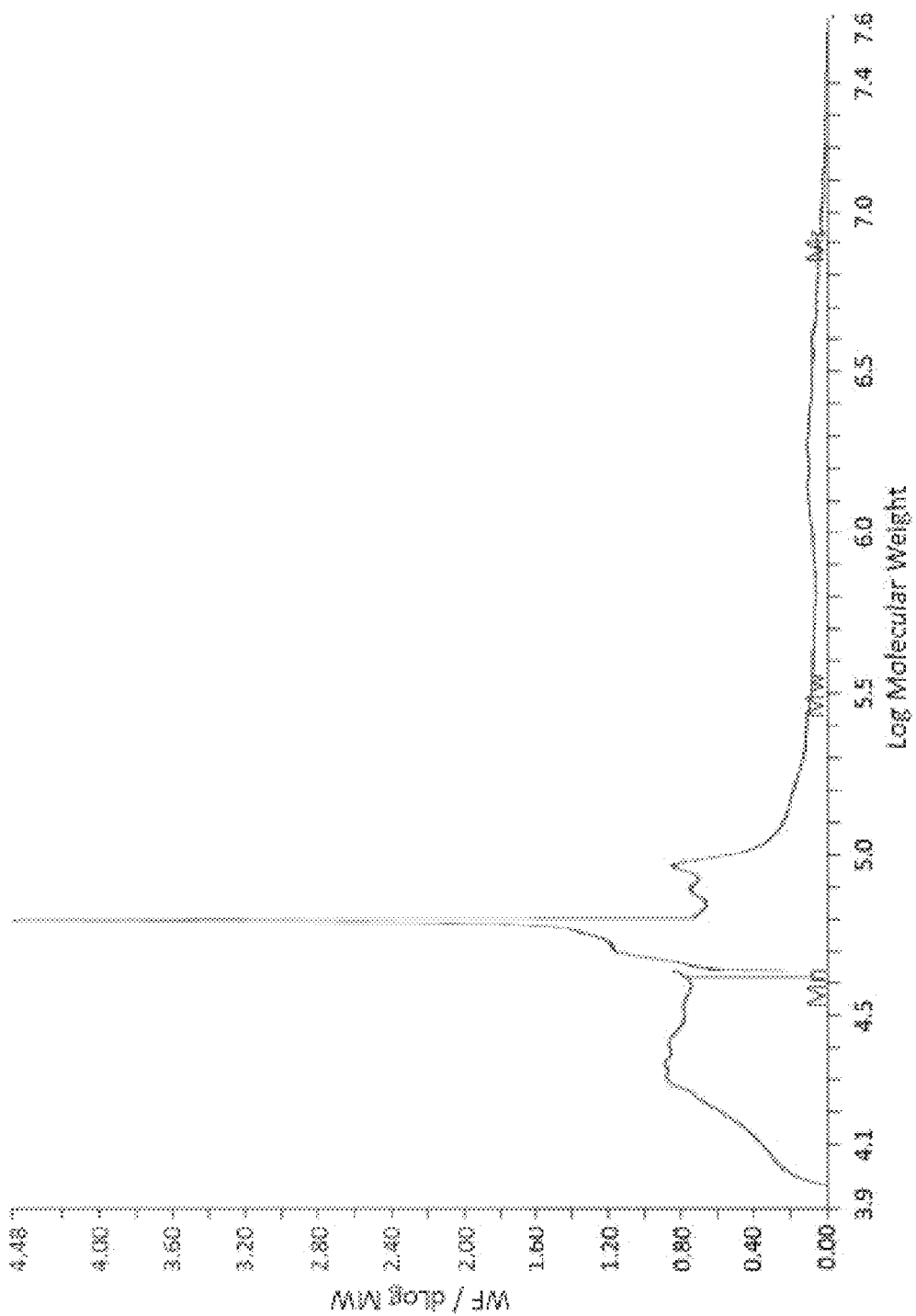
FIG. 4 shows the graph of weight fraction (WF)/dLog molecular weight (MW) vs. log molecular weight (MW) for *H. sinensis* polysaccharide sub-fraction CS-1.
Figure 5:
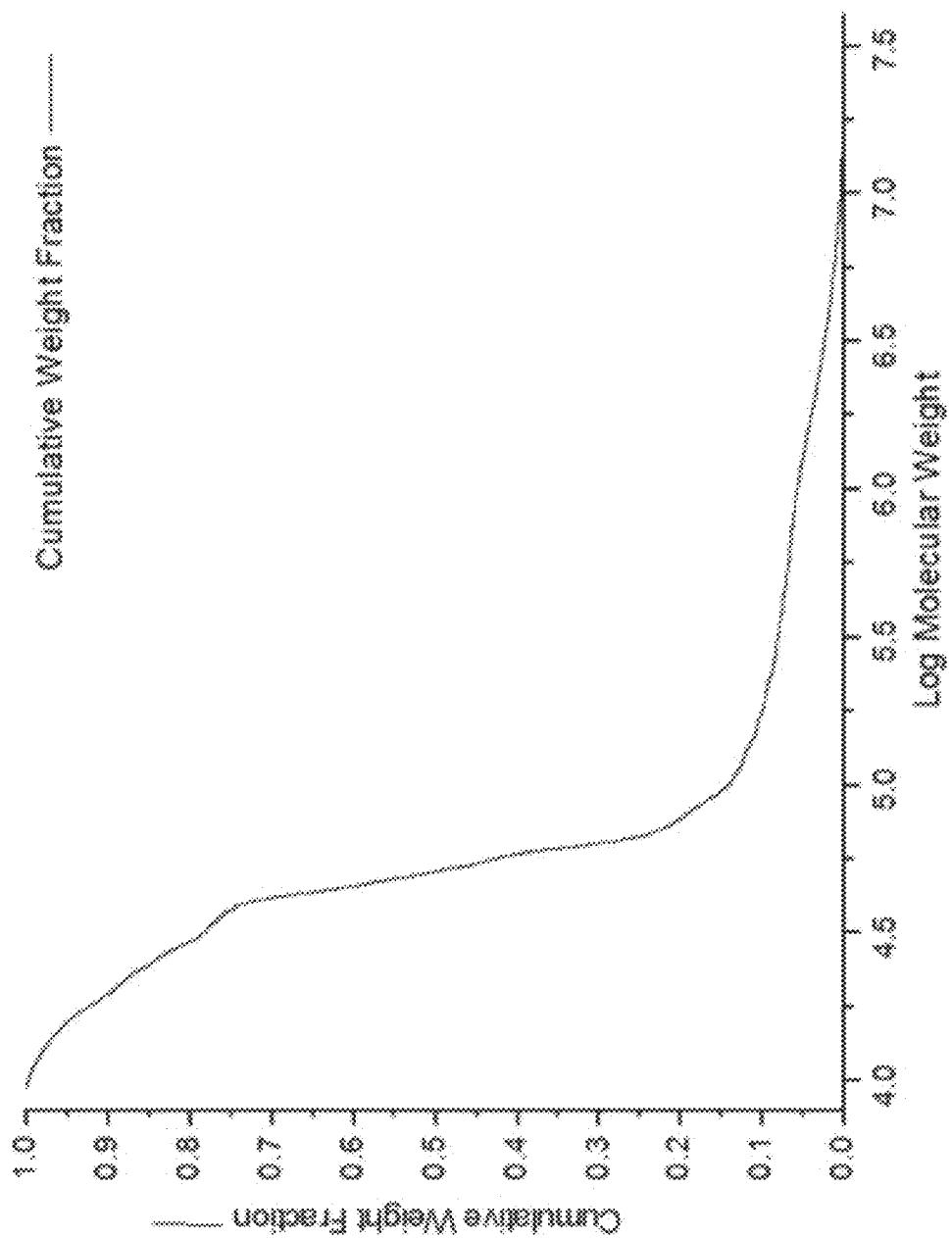
FIG. 5 shows the graph of cumulative weight fraction vs. log molecular weight for *H. sinensis* polysaccharide sub-fraction CS-1.
Figure 6A:
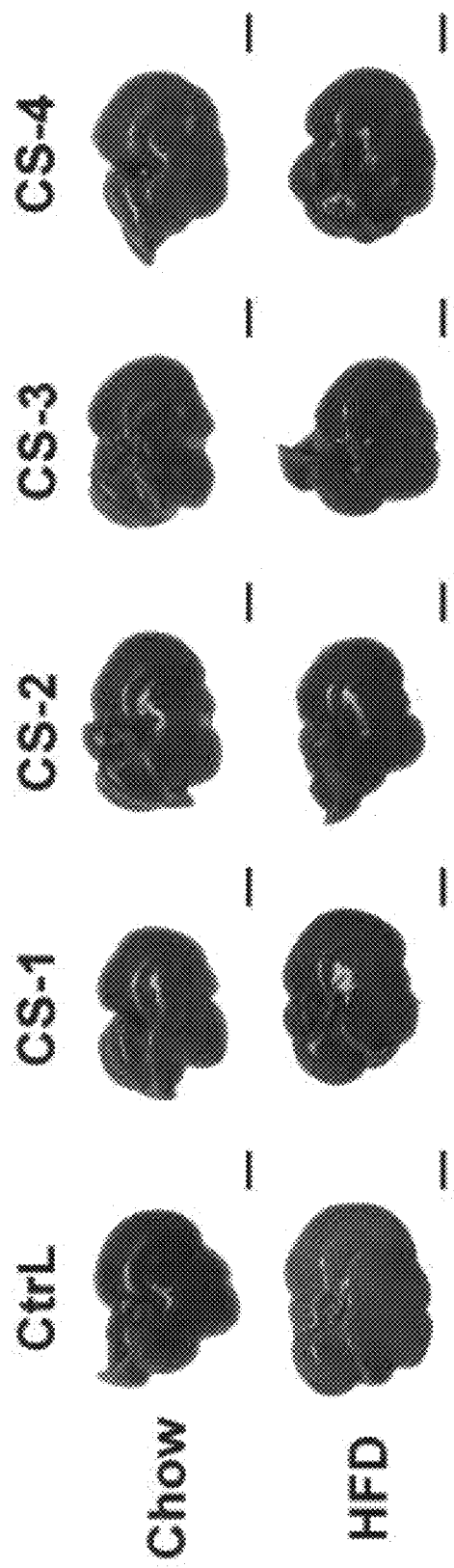
Figure 6B:
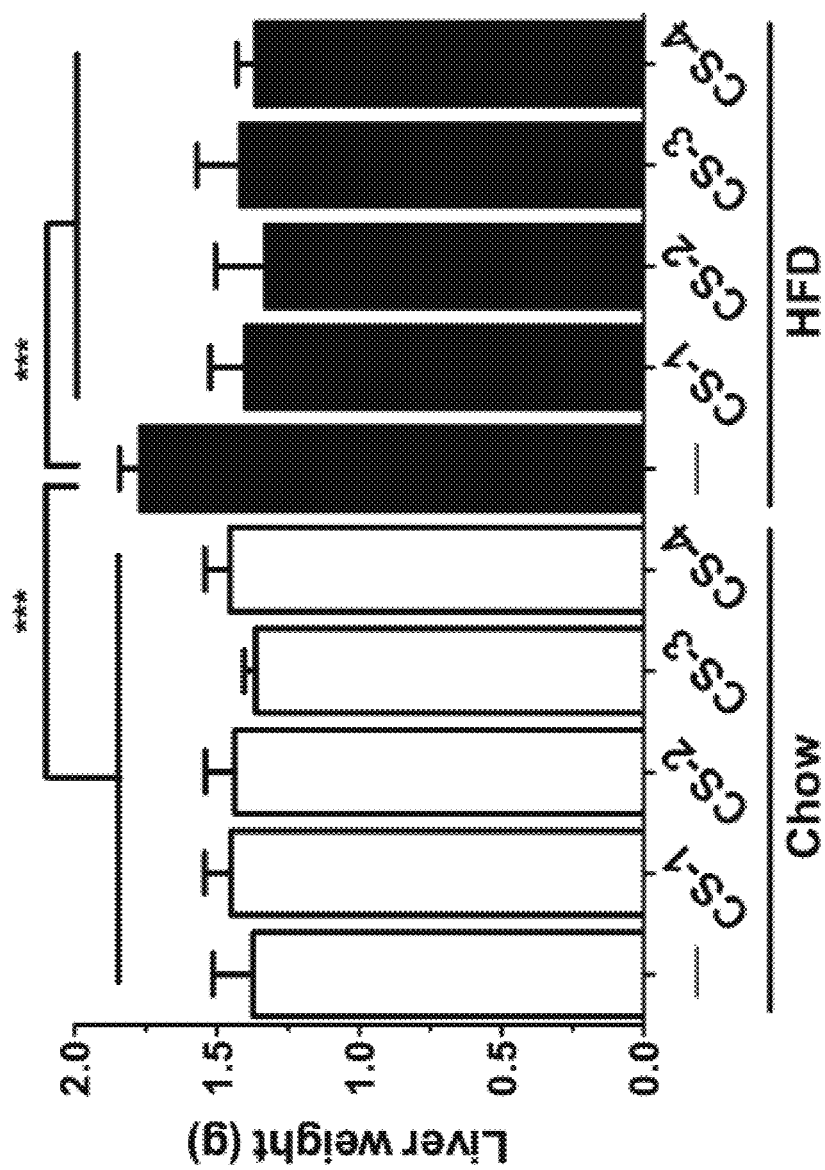
Figure 6D:
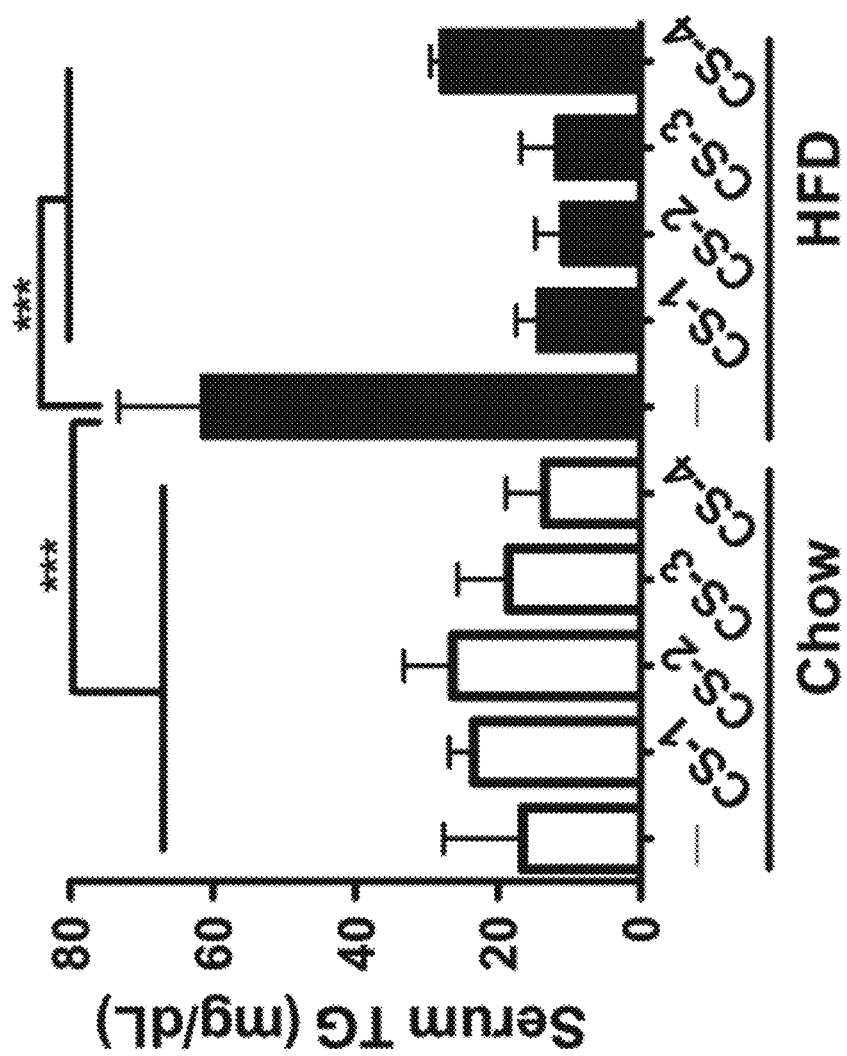
Figure 6E:
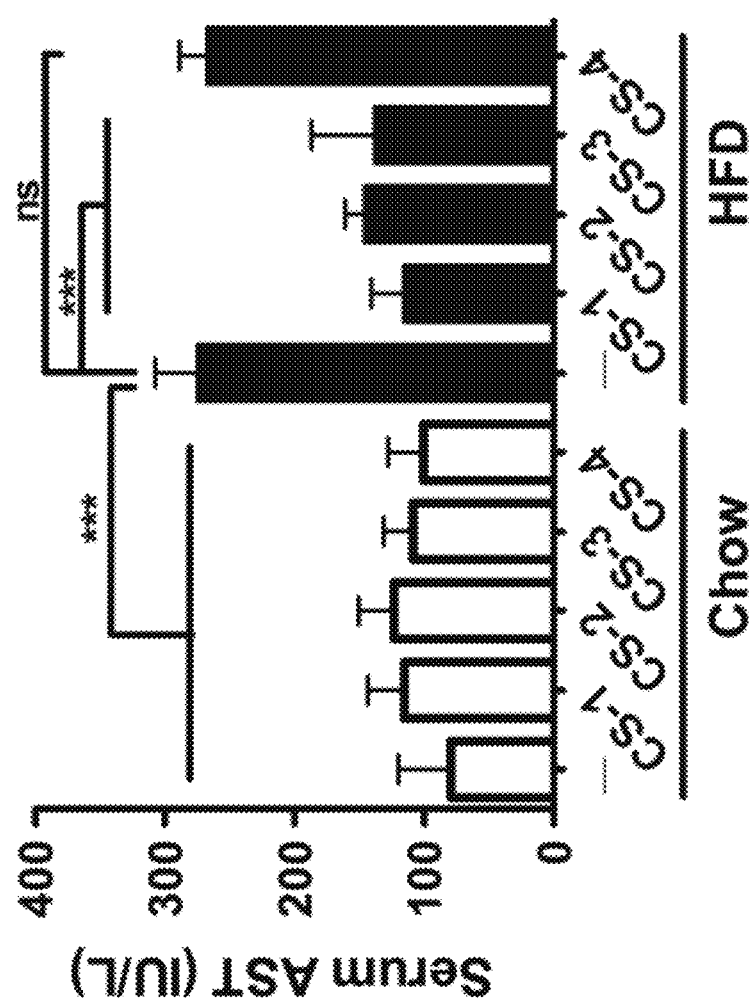

Mp: molecular weight at peak maximum, which is measured at the point of the molecular weight distribution maximum Mi: molecular weight of a chain
Ni: number of chains of that molecular weight Molecular weight analysis of the CS-1 sub-fraction (total water-soluble polysaccharide of 4 mg/mL) is performed using the GPC/SEC system; refractive index (RI) and light scattering (LS) data are obtained (FIG. 3). The polysaccharide molecular weight distribution is calculated using Viscotek OmniSEC software (FIG. 4) and the cumulative weight fraction is determined (FIG. 5).

The cumulative weight fraction values of CS-1 at 0.95 (5%) and 0.05 (95%) correspond to molecular weights of 15,776 Da and 1,231,969 Da, respectively. Polysaccharides between 15,776 Da and 1,231,969 Da thus represent approximately 90% of total polysaccharide weight of the sub-fraction. The polydispersity index (Mw/Mn) is measured as 7.475. Table 5 shows a comparison of the molecular weights of the CS-1 and CS-2 polysaccharide sub-fractions.

TABLE 5

Molecular weight comparison of the CS-1 and CS-2 sub-fractions

| Parameter | CS-1 | CS-2 |
|---|---|---|
| Mn (Daltons) | 41,731 | 38,842 |
| Mw (Daltons) | 311,921 | 49,215 |
| Mz (Daltons) | 7,589,000 | 79,949 |
| Mw/Mn (Polydispersity index) | 7.475 | 1.267 |
| MW of 5% of cumulative WF (Daltons) | 15,776 | 22,563 |
| MW of 95% of cumulative WF (Daltons) | 1,231,969 | 109,219 |

MW: molecular weight

Example 2

Effects of *H. sinensis* Polysaccharide Sub-Fractions on Signs of Fatty Liver Disease in HFD-Fed Mice FIG. 6 shows the effects of *H. sinensis* polysaccharide sub-fractions on experimental fatty liver disease induced in mice by feeding with HFD. Male C57BL/6 mice (n=10 per group) are fed with either chow (13.5% of energy from fat) or HFD (60% of energy from fat) and supplemented with 100 μL of polysaccharide sub-fraction (CS-1, CS-2, CS-3, or CS-4) or double-distilled water for 3 months by intragastric gavage. HFD feeding induces signs of fatty liver disease, including increase of liver size (FIG. 6A), liver weight (FIG. 6B), and the size and number of liver lipid vacuoles (FIG. 6C), as well as increased levels of serum TG (FIG. 6D) and AST (FIG. 6E), compared to chow-fed mice. Notably, treatment of HFD mice with CS-1, CS-2 and CS-3 for 3 months reduces liver size (FIG. 6A), liver weight (FIG. 6B), and the size and number of lipid vacuoles (FIG. 6C), as well as serum TG (FIG. 6D) and AST levels (FIG. 6E) compared to control HH mice. In comparison, *H. sinensis* polysaccharide sub-fraction CS-4 reduces liver size (FIG. 6A), liver weight (FIG. 6B), lipid vacuolization (FIG. 6C), and serum TG levels (FIG. 6D) compared to control HFD mice, but this sub-fraction produces non-significant results on AST levels (FIG. 6E). In addition, the effects of CS-4 on TG levels are less pronounced than those produced by CS-1, CS-2 and CS-3 sub-fractions (FIG. 6D).

Based on the concentration of polysaccharides found in each sub-fraction (CS-1, 0.35 g/100 mL; CS-2, 0.53 g/100 mL; CS-3, 0.13 g/100 mL), we calculate the effective amount of polysaccharide sub-fraction that reduces signs of fatty liver disease in the treated mice (which have an average body weight of 30 g): 0.00035 g of CS-1/mouse; 0.00053 g of CS-2/mouse; and 0.00013 g of CS-3/mouse. By extension, the effective dosage of *H. sinensis* polysaccharide sub-fraction reducing fatty liver disease in a human subject (with a body weight of 70 kg) is estimated as follows: 0.82 g of CS-1/subject; 1.24 g of CS-2/subject; and 0.30 g of CS-3/subject. In other words, the effective dosage of *H. sinensis* polysaccharide sub-fraction in a human subject is: 0.012 g/kg (CS-1), 0.018 g/kg (CS-2), and 0.0043 g/kg (CS-3).

The present invention provides *H. sinensis* polysaccharide sub-fractions, which can reduce signs of fatty liver disease in mammals. The *H. sinensis* polysaccharide sub-fractions of the present invention are therefore valuable for the development of new preventive strategies and treatments for fatty liver disease. The embodiments presented in the present disclosure are given as representative results that can be obtained with the polysaccharide sub-fractions, but they do not, however, limit the scope of the invention. It will be apparent to those skilled with the art that modifications can be made to the embodiments, without departing from the scope of the present invention and the appended claims.

What is claimed is:

1. A method for treating fatty liver disease, comprising administering an effective amount of a polysaccharide extracted from *Hirsutella sinensis* to a subject having fatty liver disease, wherein the polysaccharide is isolated from a water extract of a *H. sinensis* mycelium and contains at least mannose, galactose, and glucose wherein a weight ratio of mannose, galactose, and glucose is 50:23:12 to 51:24:13.

2. The method of claim 1, wherein the polysaccharide further contains fucose, rhamnose, arabinose, glucosamine, and galactosamine.

3. The method of claim 2, wherein a weight ratio of the fucose, rhamnose, arabinose, glucosamine, galactose, glucose, mannose, and galactosamine in the polysaccharide is 3:3:1:4:23:12:50:0.2 to 4:4:2:5:24:13:51:0.6.

4. The method of claim 1, wherein the polysaccharide has a molecular weight ranging from 15,776 Da to 1,231,969 Da, and a polydispersity index (Mw/Mn) of 7.475.

5. The method of claim 1, wherein an average molecular weight of the polysaccharide is 312 kDa.

6. The method of claim 1, wherein the polysaccharide reduces liver size, liver weight, the size and number of liver lipid vacuoles, serum triglycerides and serum aspartate aminotransferase levels of the subject.

7. The method of claim 1, wherein the effective amount of the polysaccharide is from 0.001 mg/kg to 1 g/kg.

8. The method of claim 1, wherein the effective amount of the polysaccharide is 0.0646 g per kilogram of body weight.

* * * * *